United States Patent [19]

Fannin et al.

[11] Patent Number: 4,615,843

[45] Date of Patent: Oct. 7, 1986

[54] TREATMENT OF HYDROCARBON SOLUTIONS OF DIALKYLMAGNESIUM COMPOUNDS TO REDUCE THE CONTENT OF SOLUBLE CHLORIDE-CONTAINING COMPLEXES

[75] Inventors: Loyd W. Fannin, Dickinson; Clark C. Crapo, Houston; Dennis L. Deavenport, Seabrook, all of Tex.

[73] Assignee: Texas Alkyls, Inc., Deer Park, Tex.

[21] Appl. No.: 647,556

[22] Filed: Sep. 5, 1984

[51] Int. Cl.$^4$ ................................................ C07F 3/02
[52] U.S. Cl. ................................................ 260/665 R
[58] Field of Search ................................... 260/665 R

[56] References Cited

U.S. PATENT DOCUMENTS

| | | | |
|---|---|---|---|
| 3,646,231 | 2/1972 | Kamienski et al. | 260/665 R |
| 3,755,478 | 8/1973 | Kamienski | 260/665 R |
| 3,766,280 | 10/1973 | Kamienski et al. | 260/665 R |
| 3,822,219 | 7/1974 | Kamienski et al. | 502/153 |
| 4,069,267 | 1/1978 | Kamienski et al. | 260/665 R |
| 4,127,507 | 11/1978 | Fannin et al. | 260/665 R X |
| 4,128,501 | 12/1978 | Smith et al. | 502/153 |
| 4,299,781 | 11/1981 | Fannin et al. | 260/429 R X |
| 4,325,840 | 4/1982 | Malpass | 502/153 |
| 4,342,708 | 8/1982 | Sakurai et al. | 260/665 R |
| 4,455,387 | 6/1984 | McKinnie et al. | 260/665 R X |

OTHER PUBLICATIONS

Kamienski et al., J. Org. Chem. 34 (4), pp. 1116–1120 (1969).

Mole et al., Organoaluminum Compounds, Elsevier pp. 177–182 (1973).

Malpass Specialty Chemicals, vol. 3 (4) pp. 6–27 (1983).

Primary Examiner—Helen M. S. Sneed
Attorney, Agent, or Firm—Joel G. Ackerman

[57] ABSTRACT

Post-precipitation of solids from a hydrocarbon solution of an organomagnesium compound is prevented by addition of an appropriate amount of an alkyllithium compound.

16 Claims, No Drawings

TREATMENT OF HYDROCARBON SOLUTIONS OF DIALKYLMAGNESIUM COMPOUNDS TO REDUCE THE CONTENT OF SOLUBLE CHLORIDE-CONTAINING COMPLEXES

BACKGROUND OF THE INVENTION

This invention pertains to the treatment of hydrocarbon solutions of hydrocarbon-soluble organomagnesium compounds, particularly dialkylmagnesium compounds.

Organomagnesium compounds of the dialkylmagnesium type are prepared in general by reaction of magnesium metal with one or more alkyl halides (according to the nature of the desired product); the process is generally conducted in a hydrocarbon solvent. Such dialkylmagnesium compounds have the general formula $R_2Mg$ in which the groups R may be identical or different alkyl groups. Not all dialkylmagnesium compounds having this general formula, however, are hydrocarbon soluble. Compounds such as dimethyl-, diethyl-, dipropyl- and di-n-butylmagnesium are not hydrocarbon soluble. On the other hand, compounds having $C_5$ alkyl or higher groups attached to the magnesium are hydrocarbon soluble. Additionally, some compounds having a mixture of lower alkyl groups attached to the magnesium are hydrocarbon soluble. These include n-butylethylmagnesium (U.S. Pat. No. 4,127,507), n-butylmethylmagnesium (U.S. Pat. No. 4,222,969) and n-propylmethylmagnesium (U.S. Pat. No. 4,207,207).

When hydrocarbon soluble dialkylmagnesium products are prepared by the reaction of alkyl halides with metallic magnesium in a hydrocarbon solvent, solids are formed which may be recovered by conventional techniques such as centrifugation, decanting or filtration. These solids comprise primarily magnesium chloride and unreacted magnesium metal. The resulting hydrocarbon solution of the dialkylmagnesium can then be diluted or concentrated as desired, depending on the ultimate concentration desired for purposes of reactivity, viscosity or economic considerations. If the solution is viscous, a viscosity reducing agent such as a trialkylaluminum compound may be included.

However, it has now been discovered that additional solids may later form in the thus separated hydrocarbon solution of dialkylmagnesium by post-precipitation when the product is stored. The post-precipitation may occur from several days to several weeks after recovery of the product solution following filtration, decantation or centrifugation. This post-precipitation results in turbidity in the product solution and can lead to decreased activity of the product due to the presence of very fine suspended solid particles.

The solids formed by post-precipitation can be removed by permitting the product to stand in storage for a sufficient time to precipitate these later formed solids, followed by a final filtration step just prior to shipping the product. Such a technique can produce stable, clear solutions, but this requires the product to be held in storage for a period of at least several additional weeks before shipping, and the final filtration involves additional processing which, of course, increases the cost of production.

SUMMARY OF THE INVENTION

This invention comprises a method for treating hydrocarbon solutions of hydrocarbon soluble dialkylmagnesium compounds to reduce the content of soluble chloride-containing complexes therein, which comprises contacting the hydrocarbon solution with a quantity, with respect to the soluble chloride, of an alkyllithium compound, sufficient to reduce the concentration of soluble chloride-containing complexes to below that at which postprecipitation occurs, by precipitation of soluble chloride as lithium chloride, and removing the precipitated lithium chloride from the solution.

DETAILED DESCRIPTION OF THE INVENTION

On investigation it was determined that the post-precipitation of solids results from the presence in the hydrocarbon solution (after filtration of the precipitated solids from the original reaction) of hydrocarbon soluble chloride-containing complexes which are believed to have the general formula $$XR_2Mg \cdot {}^4/Y(RMgCl)Y;$$

where the value of X is much greater than the value of Y. These hydrocarbon soluble chloride-containing complexes are believed to produce post-precipitation via an equilibrium involving a redistribution reaction of the type $$XR_2Mg \cdot {}^4/y(RMgCl)_y \rightarrow (X+1)R_2Mg + MgCl_2 \cdot 2RMgCl$$

in which the complex $MgCl_2 \cdot 2RMgCl$ is insoluble and precipitates from the solution.

The problem of post-precipitation can be effectively prevented by reducing the concentration of soluble chloride-containing complexes to a level below that at which post-precipitation occurs, by contacting the hydrocarbon solution with an appropriate amount of an alkyllithium compound to remove a portion of the soluble chloride by precipitation as lithium chloride. The alkyllithium compound has the formula R'Li in which R' is an alkyl group having from 1 to 20 carbon atoms, preferably 1 to 10 carbon atoms. The alkyllithium compound itself is at least partially soluble, and preferably soluble, in hydrocarbon solvents (particularly in paraffinic solvents). Butyllithiums such as n-butyl- and t-butyllithium are convenient for use in this process.

The concentration of soluble chloride-containing complexes at which post-precipitation occurs will vary somewhat, according to the alkyl groups in the dialkylmagnesium compound, the particular hydrocarbon solvent used, and the temperature, but can readily be determined empirically for a given composition or given conditions. For instance, the solubility of these complexes tends to be higher in aromatic solvents than in aliphatic ones. Also, as would be expected, the solubility increases with temperature. For a system as used in the samples which follow, containing n-butylethylmagnesium in n-heptane, post-precipitation would generally occur at ambient temperature (about 25° C.) at soluble chloride concentrations of about 0.05–0.06 weight percent.

The alkyllithium compound is generally added in an amount of from about 50% to about 300% of the stoichiometric amount, based on soluble chloride in the hydrocarbon solution. Preferably the alkyllithium is used in about 75–300% of stoichiometric, most preferably about 100–200%. The concentration of soluble chloride is readily determinable by conventional methods, such as Volhard titration with silver nitrate.

The alkyllithium compound is added to the hydrocarbon solution of the organomagnesium compound subsequent to its production from magnesium and the alkyl halide or halides. The alkyllithium compound may be added either before or after removal of solids resulting from the production of the dialkylmagnesium compound are removed from the hydrocarbon solution. When the alkyllithium is added after separation of the solids, care should be taken to add as little excess over the stoichiometric amount as feasible, or to add less than the stoichiometric amount, to minimize the lithium content of the resulting hydrocarbon solution of dialkylmagnesium.

Preferably, however, the alkyllithium compound is added prior to the removal of solids. At this time the ratio of magnesium chloride in the solids to soluble chloride complexes in the solution is generally on the order of 100:1. It is surprising, in this situation, that the alkyllithium compound, especially when added in such small amounts, has any substantial effect on the soluble chloride content, since it is known in the art (U.S. Pat. No. 4,069,267, for instance) that alkyllithium compounds can react with solid magnesium chloride. However, we have found that the alkyllithium reacts preferentially with the soluble chloride-containing complexes rather than with solid magnesium chloride.

When the alkyllithium compound is added before the solids are removed, any excess alkyllithium will be consumed by reaction with magnesium chloride in the solids, producing insoluble lithium chloride. This produces the added advantage of ensuring that little or no lithium is introduced into the hydrocarbon solution of dialkylmagnesium.

The alkyllithium compound reacts with the soluble chloride-containing complex to produce insoluble lithium chloride plus soluble dialkylmagnesium product. This provides a second reason for the preference for adding the alkyllithium compound to the dialkylmagnesium product before the solids are removed—the lithium chloride can be filtered off with the solids produced by the reaction, so that a second filtration step would not be required. However, as mentioned previously, the alkyllithium compound can be added after filtration of the solids from the original reaction product, and the insoluble lithium chloride removed by conventional filtration, decanting or centrifugation techniques.

Hydrocarbon solutions of some dialkylmagnesium compounds are relatively viscous. In such cases, the desired product may also contain a viscosity reduction agent of known type, such as a trialkyl aluminum compound. Again, care should be taken to avoid the use of excess alkyllithium when such viscosity reduction agents are present and the solids have been separated, as the alkyllithium may form a complex with the viscosity reduction agent which could reduce its effectiveness and cause the viscosity of the solution to increase and also result in the presence of lithium in the dialkylmagnesium product.

The process of the present invention is further illustrated by the following examples.

EXAMPLE 1

A ten weight percent (10 wt. %) solution of n-butylethylmagnesium (BEM) in n-heptane was prepared as follows. A pressure bottle was prepared and heated in an oil bath thermostatically controlled at 115° C. The pressure bottle was equipped with a stirrer. Magnesium powder (18.0 grams, 0.0740 mole) was charged to the pressure bottle and allowed to heat at about 110° C. under a purge of nitrogen. The bottle was removed from the bath and 200 grams (g) dry n-heptane was added. A small amount (0.2 g) of triethylaluminum was injected into the heptane under nitrogen atmosphere to serve as an activator and viscosity reducer. After the pressure bottle was established as the bath temperature, a mixture of ethyl chloride (23.9 g, 0.370 mole) and n-butyl chloride (34.2 g, 0.369 mole) was slowly charged. Temperature was held at 115°–120° C. The addition took 1.5 hours; the pressure rose to about 35 psig. Some 30 minutes was allowed for completion of the reaction, and the slurry was allowed to settle while cooling. Analysis of the clear liquid gave the following results: Mg, 2.82 wt. %; Al, 0.02 wt. %; Cl, 0.11 wt. %. Analysis of the hydrolysis gas gave a composition of 50.9 mole percent n-butane and 49.1 mole % ethane.

The product was divided into two portions. One portion was centrifuged, and the clear liquid was analyzed by titration with silver nitrate and found to contain 0.11 wt. % of soluble chloride. To the other portion was added 0.037 g (0.0006 mole), or approximately twice the stoichiometric quantity, of tertiary butyllithium, while the slurry was being stirred. After 30 minutes the stirring was stopped and the container was centrifuged. Analysis showed 0.04 wt. % soluble chloride remaining in the clear liquid. The remaining contents of the vial were stirred for 25 hours and reanalyzed after again centrifuging. This final analysis showed 0.02 wt. % of soluble chloride. The other portion, which had not been treated with the alkyllithium was again analyzed, and the analysis showed no charge in soluble chloride content—it remained at 0.11 wt. %.

EXAMPLE 2

Another solution of n-butylethylmagnesium in n-heptane was prepared and separated from the solids. The solution contained approximately 10 wt. % n-butylethylmagnesium, 0.09 wt. % triethylaluminum, and 0.08 wt. % of soluble chloride. To about 100 g of this solution there was added about 1.0 g of a solution in n-pentane of tertiary butyllithium (1.58 wt. % Li). The previously clear n-butylethylmagnesium became turbid immediately, without heating. The next day, the treated solution showed a turbidity value of 7 as compared with 0 for the untreated solution. A sample of the treated solution was centrifuged and analyzed for soluble chloride. The analysis showed that the soluble chloride content had decreased to 0.02 wt. %.

EXAMPLE 3

The magnesium alkyl solution used in this example was a clear solution of n-butylethylmagnesium/triethylaluminum in n-heptane which contained 2.25 wt. % magnesium, 0.06 wt. % aluminum, and 0.04 wt. % soluble chloride. To 132.3 g of this solution there was added 2.0674 g of a solution of tertiary butyllithium (1.58 wt. % Li) in n-pentane. Upon addition of lithium alkyl, the solution became turbid and the viscosity increased markedly. The amount of lithium alkyl added comprised 0.0032 mole in excess of stoichiometric—this was about equivalent to the content of triethylaluminum (0.0029 mole) present in the solution. Analysis of the centrifuged sample after treatment showed 2.25 wt. % magnesium, 0.04 wt. % aluminum, and no chlorine. Apparently the excess lithium alkyl formed a complex with the triethylaluminum, rendering it ineffective as a viscosity reducer.

To confirm this theory, a small amount of anhydrous magnesium chloride was added to the viscous solution, and the viscosity of this solution became immediately reduced to about the same as that of the original sample; this occurred due to the reaction of magnesium chloride with the alkyllithium, precipitating lithium chloride, and removing lithium from the solution.

EXAMPLE 4

In order to study the effects of temperature and lithium alkyl concentration on chloride removal, 16 sample bottles of n-butylethylmagnesium/heptane—$MgCl_2$ slurry were collected from freshly prepared product which was made in a large-scale reactor by the general procedure described in Example 1. Initially, the soluble chloride in a centrifuged sample was found to be 0.17 wt %. The samples were allowed to age for nine days prior to testing, after which time the soluble chloride had decreased to 0.13 wt %.

One of the sample bottles was placed in each of five baths maintained at the following temperatures: 10°, 22°, 40° 55° and 70° C. To each bottle was added sufficient n-butyllithium to give a nominal Li:Cl stoichiometry of 1:1. For example, 0.37 ml (0.24 g of n-butyllithium) of a 10.2 molar n-butyllithium/hexane solution was added to 128.4 g n-butylethylmagnesium/heptane—$MgCl_2$ slurry containing about 104 g of liquid n-butyllithium. The sample bottles were allowed to equilibrate in the baths for 30 minutes prior to adding n-butyllithium, and then 15 minutes reaction time was allowed. Samples were taken from the bottles, centrifuged for 5 minutes and then a weighed portion of the clear liquid was hydrolyzed immediately for analysis.

This set of tests was repeated at nominal Li:Cl stoichiometries of 2:1 and 3:1. Results shown in Table I indicate that a larger excess of lithium alkyl is required at higher temperatures to obtain effective chloride reduction.

TABLE I

| Residual Soluble Chloride Found (wt %) at Various Ratios of n-Butyllithium:Initial Chloride[a] | | | |
|---|---|---|---|
| Temperature, °C. | 1:1 | 2:1 | 3:1 |
| 10 | 0.03 | 0.02 | 0.02 |
| 22 | 0.04 | 0.02 | 0.01 |
| 40 | 0.04 | 0.03 | 0.02 |
| 55 | 0.06 | 0.04 | 0.03 |
| 70 | 0.07 | 0.06 | 0.05 |

[a]Initial soluble chloride was 0.13 wt % at ambient temperature.

What is claimed is:

1. A method for treating a hydrocarbon solution of a hydrocarbon soluble dialkylmagnesium compound to reduce the content of soluble chloride-containing complexes therein which comprises contacting the hydrocarbon solution with a quantity, with respect to the soluble chloride, of an alkyllithium compound, sufficient to reduce the concentration of soluble chloride-containing complexes to below that at which post-precipitation occurs, by precipitation of soluble chloride as lithium chloride, and subsequently removing the precipitated lithium chloride from the solution.

2. A method according to claim 1 in which the hydrocarbon solution is contacted with the alkyllithium compound in the presence of solid magnesium chloride.

3. A method according to claim 1 in which the dialkylmagnesium compound is n-butylethylmagnesium.

4. A method according to claim 1 in which the alkyllithium compound is added in an amount of from about 50% to about 300% of the stoichiometric amount, based on soluble chloride in the hydrocarbon solution.

5. A method according to claim 4 in which the amount of alkyllithium compound added is from about 75% to about 300% of stoichiometric.

6. A method according to claim 4 in which the amount of alkyllithium compound added is from about 100 to about 200% of stoichiometric.

7. A method according to claim 1 in which the alkyllithium compound is one having from 1 to 20 carbon atoms in the alkyl group.

8. A method according to claim 1 in which the alkyllithium compound has 4 carbon atoms in the alkyl group.

9. A method according to claim 1 in which the alkyllithium compound is n-butyllithium.

10. A method according to claim 1 in which the alkyllithium compound is tertiary-butyllithium.

11. In a method for production of hydrocarbon solutions of hydrocarbon soluble dialkylmagnesium compounds by reaction of metallic magnesium with one or more alkyl halides in a hydrocarbon solvent, and in which the hydrocarbon solution of the desired dialkylmagnesium compound is separated from solids formed during the reaction, the improvement comprising contacting the reaction product, prior to the separation of the hydrocarbon solution from the solids, with a quantity, with respect to soluble chloride-containing complexes present in the product, of an alkyllithium compound sufficient to reduce the concentration of soluble chloride-containing complexes to below that at which post-precipitation occurs, by precipitation of soluble chloride, to precipitate lithium chloride, and subsequently separating the hydrocarbon solution of the dialkylmagnesium compound from the solid materials.

12. A process according to claim 11 in which the dialkylmagnesium compound is n-butylethylmagnesium, and the alkyl halides are n-butyl chloride and ethyl chloride, respectively.

13. A process according to claim 11 in which an alkylaluminum viscosity reducing agent is present in the process and in the hydrocarbon solution.

14. A method according to claim 11 in which the alkyllithium compound is added in an amount of from about 50% to about 300% of the stoichiometric amount, based on soluble chloride ion in the hydrocarbon solution.

15. A method according to claim 14 in which the amount of alkyllithium compound added is from about 75% to about 300% of stoichiometric.

16. A method according to claim 14 in which the amount of alkyllithium compound added is from about 100 to about 200% of stoichiometric.

* * * * *